United States Patent
Otake et al.

(10) Patent No.: US 11,766,542 B2
(45) Date of Patent: Sep. 26, 2023

(54) CATHETER

(71) Applicant: TERUMO KABUSHIKI KAISHA, Tokyo (JP)

(72) Inventors: Yuya Otake, Fujinomiya (JP); Kota Hamuro, Fujinomiya (JP); Koichiro Tashiro, Tokyo (JP); Mariko Maruyama, Fujinomiya (JP); Tetsuya Fukuoka, Hadano (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 336 days.

(21) Appl. No.: 17/110,943

(22) Filed: Dec. 3, 2020

(65) Prior Publication Data

US 2021/0085914 A1   Mar. 25, 2021

Related U.S. Application Data

(60) Division of application No. 15/265,042, filed on Sep. 14, 2016, now Pat. No. 10,874,828, which is a (Continued)

(30) Foreign Application Priority Data

Mar. 18, 2014   (JP) ................................ 2014-055658

(51) Int. Cl.
  *A61M 25/00*   (2006.01)
(52) U.S. Cl.
  CPC ... *A61M 25/005* (2013.01); *A61M 2025/0025* (2013.01)
(58) Field of Classification Search
  CPC .............. A61M 25/005; A61M 2025/0025
  See application file for complete search history.

(56) References Cited

U.S. PATENT DOCUMENTS

2006/0229589 A1   10/2006   Itou et al.
2014/0276284 A1   9/2014   Mansur et al.

FOREIGN PATENT DOCUMENTS

DE   202012103439 U1   10/2012
EP   1917987 A2   5/2008
(Continued)

OTHER PUBLICATIONS

"Transradial Intervention of Iliac and Superficial Femoral Artery Disease is Feasible", J Interv Cardiol, vol. 21, 2008 (month unknown), pp. 385-387.

(Continued)

*Primary Examiner* — Bradley J Osinski
(74) *Attorney, Agent, or Firm* — BUCHANAN INGERSOLL & ROONEY PC

(57) ABSTRACT

A catheter that includes an inner layer forming the inner surface of a tubular catheter main body having a lumen, an outer layer forming the outer surface of the catheter main body, and multiple reinforcements embedded between the inner surface and the outer surface. The inner diameter of the catheter main body is D1, the outer diameter is D2, the wall thickness is T1, a thickness of each reinforcement is T2, an effective width of each reinforcement is W, and a total number of the multiple reinforcements is N. The catheter satisfies Expressions (1), (2), and (3):

| | |
|---|---|
| 0.050 mm≤$T1$≤0.100 mm | Expression (1) |
| $T2/T1$≥0.25 | Expression (2) |
| 60,000≤$(D1 \times D2 \times W \times N)/(T1^2 \times T2)$<1,000,000 | Expression (3). |

14 Claims, 6 Drawing Sheets

Related U.S. Application Data continuation of application No. PCT/JP2015/054968, filed on Feb. 23, 2015.

(56) References Cited

FOREIGN PATENT DOCUMENTS

| | | | |
|---|---|---|---|
| EP | 2213325 | A1 | 8/2010 |
| JP | 2005110721 | A | 4/2005 |
| JP | 2006288670 | A | 10/2006 |
| WO | 2009054509 | A1 | 4/2009 |
| WO | 2014049776 | A1 | 4/2014 |

OTHER PUBLICATIONS

The extended European Search Report dated Jun. 16, 2020, by the European Patent Office in corresponding European Patent Application No. 20151514.5-1132. (13 pages).

International Search Report (PCT/ISA/210) dated Jun. 2, 2015, by the Japanese Patent Office as the International Searching Authority for International Application No. PCT/JP2015/054968.

Written Opinion (PCT/ISA/237) dated Jun. 2, 2015, by the Japanese Patent Office as the International Searching Authority for International Application No. PCT/JP2015/054968.

Machine Translation of WO2009/054509, which was published Apr. 30, 2009.

CATHETER

CROSS-REFERENCES TO RELATED APPLICATIONS

This application is a divisional application of U.S. patent application Ser. No. 15/265,042 filed on Sep. 14, 2016 which is a continuation of International Application No. PCT/JP2015/054968 filed on Sep. 24, 2015, which claims priority to Japanese Patent Application No. 2014-55658 filed on Mar. 18, 2014, the entire content of all three of which is incorporated herein by reference.

TECHNICAL FIELD

The present invention relates to a catheter to be inserted into a biological lumen and a method of use, and particularly relates to a guiding catheter which guides a medical instrument such as a treatment catheter to a target site.

BACKGROUND DISCUSSION

A guiding catheter may be used to insert a treatment catheter (a dilation catheter, a stent indwelling catheter, and the like) into a biological lumen of a living body such as a blood vessel. The treatment catheter may be for performing medical treatment, diagnosis, and the like. The guiding catheter is used to guide the treatment catheter to the target site.

In order to lessen incision of a vascular insertion portion such that a burden to a patient is reduced (i.e., harm to the living body is mitigated/reduced), and to reduce friction with respect to a blood vessel, the guiding catheter is required to possess a smaller outer diameter. The treatment catheter to be inserted into the guiding catheter, however, is required to possess a larger outer diameter in order to exhibit a sufficient effect at the target site such as a treatment site (e.g., the treatment catheter needs to have a large enough outer diameter to be able to perform the treatment functions). Therefore, the guiding catheter that facilitates inserting the treatment catheter is required to be further increased in inner diameter (i.e., the guiding catheter must possess a sufficiently large inner diameter).

Recently, a technique has been conducted in which a catheter is inserted through an artery of a wrist and treatment of the coronary artery is performed by applying trans-radial intervention (TRI). When having access to an artery of the lower extremity from an artery of a wrist by applying the TRI, a problem arises because the vascular diameter of the lower extremity (the inner diameter of a blood vessel at a target site of the catheter) is greater than the vascular diameter of a wrist (the inner diameter of a blood vessel at an insertion site of the catheter). It is thus difficult to access the target site. Specifically, since the vascular diameter of the lower extremity is greater than the vascular diameter of the wrist, the inner diameter of the guiding catheter in the related art is insufficiently small. There is a problem in that the treatment catheter to be inserted into the guiding catheter cannot exhibit a sufficient effect at the target site inside a blood vessel. In order to treat a blood vessel of the lower extremity by using the TRI technique, there is thus a demand for a guiding catheter that possesses a larger inner diameter and a smaller outer diameter relative to known catheters.

However, when the guiding catheter is increased in inner diameter and decreased in outer diameter, the wall thickness decreases (i.e., the wall becomes thinner). When the guiding catheter has a decreased wall thickness, a tube wall of the guiding catheter is weakened. Squashing or bending (a kink) is thus likely to occur. Therefore, in a case where the guiding catheter possesses a relatively thin wall, a method of improving kink resistance of the guiding catheter (such as adjusting the quantity or the shape of reinforcements embedded between an inner layer and an outer layer of the guiding catheter) is adopted.

For example, Japanese Patent Application Publication No. 2006-288670 discloses a method in which the inner diameter of the guiding catheter is increased relative to the outer diameter and a kink is unlikely to occur by setting the ratio of the thickness of each reinforcement to the wall thickness of the guiding catheter and the ratio of the cross-sectional area of each reinforcement to the cross-sectional area of the guiding catheter within predetermined ranges.

The guiding catheter is able to guide a medical instrument such as the treatment catheter to a target site. Even when a kink occurs at a portion of guiding catheter inside a blood vessel which is complicatedly curved (i.e., possesses the shape of a tortuous curve), it is preferable that a medical instrument inserted into the guiding catheter can pass through the kinked portion of the guiding catheter. Therefore, even when a kink occurs, the guiding catheter needs to relieve the kink and to allow a medical instrument to be inserted into the lumen. However, in Japanese Patent Application Publication No. 2006-288670 there is no explanation regarding the physical performance of the guiding catheter necessary for when a kink occurs. There is thus a demand for a guiding catheter having a function described above.

The inventors have intently endeavored to realize various types of performance required in the above-described catheter and have resultantly come to invent an optimal structure.

SUMMARY

The catheter possesses an inner diameter that is significantly large relative to the outer diameter of the catheter and in which maneuverability (i.e., crossability) of a medical instrument within a lumen of the catheter can be favorably ensured even in a case where a kink occurs.

One aspect of the disclosure here involves a method that comprises inserting a catheter into a blood vessel of an arm of a living body. The catheter comprises: an inner layer forming an inner surface of a tubular catheter main body having a lumen; an outer layer forming an outer surface of the catheter main body, with the catheter main body possessing an inner diameter, an outer diameter and a wall thickness; multiple reinforcements embedded between the inner surface and the outer surface of the catheter main body; and the catheter satisfying Expressions (1), (2), (3), (4), (5), and (6) below:

$$0.050 \text{ mm} \leq T1 \leq 0.100 \text{ mm} \quad \text{Expression (1)}$$

$$T2/T1 \geq 0.25 \quad \text{Expression (2)}$$

$$60{,}000 \leq (D1 \times D2 \times W \times N)/(T1^2 \times T2) < 1{,}000{,}000 \quad \text{Expression (3)}$$

$$B1 = (D1/T1) \times (D2/T1) \quad \text{Expression (4)}$$

$$B2 = (W \times N)/T2 \quad \text{Expression (5)}$$

$$B = B1 \times B2 \quad \text{Expression (6),}$$

wherein the inner diameter of the catheter main body is D1, the outer diameter of the catheter main body is D2, the wall thickness of the catheter main body is T1, a thickness of each reinforcement along a radial direction of the catheter main body is T2, an effective width of each reinforcement along the circumferential direction of the catheter main body in a cross section orthogonal to an axial direction of the catheter main body is W, and a total number of the multiple reinforcements is N, the outer diameter of the catheter main body is 2.32 mm to 3 mm, and the value B is 80,000 to less than 500,000. The method further comprises advancing the catheter from the arm of the living body toward a blood vessel in a lower extremity of the living body, and positioning the distal end of the catheter in the blood vessel in the lower extremity of the living body.

According to another aspect, a method comprises inserting a catheter into a radial artery of a living body, wherein the catheter comprises: an inner layer forming an inner surface of a tubular catheter main body having a lumen, an outer layer forming an outer surface of the catheter main body, the catheter main body possessing an inner diameter, an outer diameter, a distal end, and a wall thickness, multiple reinforcements between the inner surface and the outer surface of the catheter main body, and the catheter satisfying Expressions (1), (2), and (3) below:

$0.050 \text{ mm} \leq T1 \leq 0.100 \text{ mm}$  Expression (1)

$T2/T1 \geq 0.25$  Expression (2)

$60,000 \leq (D1 \times D2 \times W \times N)/(T1^2 \times T2) < 1,000,000$  Expression (3), wherein the inner diameter of the catheter main body is D1, the outer diameter of the catheter main body is D2, the wall thickness of the catheter main body is T1, a thickness of each reinforcement along a radial direction of the catheter main body is T2, an effective width of each reinforcement along the circumferential direction of the catheter main body in a cross section orthogonal to an axial direction of the catheter main body is W, and a total number of the multiple reinforcements is N. The method additionally comprises advancing the catheter from the radial artery toward a blood vessel in a lower extremity of the living body, positioning the distal end of the catheter at a target site in the blood vessel in the lower extremity of the living body, determining a kink exists along the catheter while the distal end of the catheter is in the blood vessel in the lower extremity of the living body; and introducing a guide wire into the catheter when a kink is determined to exist along the catheter and advancing the guide wire through the kink.

In accordance with another aspect, a method involves inserting a catheter into a blood vessel of an arm of a living body, wherein the catheter comprises: an inner layer forming an inner surface of a tubular catheter main body having a lumen, an outer layer forming an outer surface of the catheter main body, the catheter main body possessing an inner diameter, an outer diameter, a distal end, and a wall thickness, multiple reinforcements between the inner surface and the outer surface of the catheter main body, and the catheter satisfying Expressions (1), (2), and (3) below:

$0.050 \text{ mm} \leq T1 \leq 0.100 \text{ mm}$  Expression (1)

$T2/T1 \geq 0.25$  Expression (2)

$60,000 \leq (D1 \times D2 \times W \times N)/(T1^2 \times T2) < 1,000,000$  Expression (3), wherein the inner diameter of the catheter main body is D1, the outer diameter of the catheter main body is D2, the wall thickness of the catheter main body is T1, a thickness of each reinforcement along a radial direction of the catheter main body is T2, an effective width of each reinforcement along the circumferential direction of the catheter main body in a cross section orthogonal to an axial direction of the catheter main body is W, and a total number of the multiple reinforcements is N. The method additionally comprises moving the catheter within blood vessels in the living body to advance the catheter from the arm of the living body toward a blood vessel in a lower extremity of the living body; and positioning the distal end of the catheter in the blood vessel in the lower extremity of the living body.

The catheter used in the method includes the catheter main body which is thin in wall thickness (i.e., relatively thin-walled). The reinforcements help ensure sufficient reinforcing (i.e., rigidity) of the catheter main body in the radial direction and the circumferential direction. Specifically, when Expression (2) is satisfied, reinforcing the catheter main body in the radial direction performed by the reinforcements is ensured. Moreover, when Expression (3) is satisfied, the shape of the catheter main body is defined so as to be a shape unlikely to be kinked, and reinforcing in the circumferential direction performed by all of the N reinforcements is ensured. Therefore, the catheter disclosed here includes reinforcements that sufficiently reinforce (i.e., provide rigidity) in the radial direction and the circumferential direction. Thus, the inner diameter of the catheter main body can be increased relative to the outer diameter. Moreover, in the catheter disclosed here, reinforcing in the radial direction and the circumferential direction is performed by the reinforcements within a predetermined range. Thus, even in a case where the catheter main body is kinked, a medical instrument can pass through the lumen of the catheter main body because a certain clearance is ensured in the lumen of the catheter. Moreover, the lumen (which becomes narrow due to a kink occurring when a medical instrument is thrust therethrough) can be widened. The medical instrument can thus pass through the lumen. Therefore, the catheter disclosed here helps ensure maneuverability of a medical instrument within the lumen of the catheter even in a case where the catheter main body is kinked.

It is preferable that the outer diameter of the catheter main body in the catheter ranges from 2 mm to 3 mm, and an effective width W of each reinforcement ranges from 0.200 mm to 0.600 mm. In this configuration, reinforcing in the circumferential direction performed by the reinforcements can be sufficiently ensured with respect to the outer diameter of the catheter main body in each of cross sections of the catheter main body. Therefore, even though the outer diameter of the catheter main body ranges from 2 mm to 3 mm, a significant inner diameter (i.e., relatively large inner diameter) of the catheter can be ensured relative to the outer diameter. Accordingly, the catheter disclosed here can be inserted into a thin biological lumen, and the burden to a patient can be reduced.

When the catheter main body is bent 180° and a kinked portion is made, in a cross-sectional shape of the kinked portion of the catheter main body at the time an angle formed by the kinked portion returns to 90°, it is preferable that spaces formed at a left end and a right end of the lumen of the catheter main body are configured to be greater than a space formed at the center of the left end and the right end of the lumen of the catheter main body. In this configuration, when the catheter is delivered to a target site inside a biological lumen, even though the catheter is kinked, the guide wire can pass through the lumen of the catheter on a distal side closer than the kinked portion via the clearances formed at the left end and the right end of the lumen at the kinked portion of the catheter. Therefore, a medical instrument can be inserted into the lumen of the catheter by utilizing the guide wire. Accordingly, there is no need for an operator to replace the catheter even though the catheter is kinked.

Therefore, a treatment time of an operator is shortened. The burden to the body of a patient can thus be reduced. Here, the angle formed by the kinked portion denotes an angle formed by the axial center of a non-kinked portion on the distal side closer than the kinked portion of the catheter main body and the axial center of a non-kinked portion on a proximal side closer than the kinked portion of the catheter main body.

In the catheter, when the catheter main body is bent 180° and a kinked portion is made, it is preferable that the lumen of the catheter main body at the kinked portion at the time an angle formed by the kinked portion returns to 90° is configured to allow a guide wire having an outer diameter of 0.89 mm to be inserted through the lumen. In this configuration, when the catheter disclosed here is delivered to a target site inside a biological lumen, even though the catheter may be kinked, a medical instrument such as the guide wire can be inserted into the lumen of the catheter without replacing the kinked catheter. Therefore, a treatment time of an operator is shortened, and a burden to the body of a patient can be reduced.

It is preferable that a distance between a turned-back end of a loop and a plate is configured to be equal to or less than 45 mm at the time the loop is made by causing the catheter main body to pass through two penetration holes that are parallel to each other, have diameters of 2.8 mm, and are open at portions of which the center-to-center distance is 10 mm in the plate having a thickness of 10 mm in water of 37° C. and a kink occurs by pulling one end of the catheter main body. In this configuration, kink resistance of the catheter main body is enhanced. Even in a case where the catheter main body is kinked, maneuverability of a medical instrument with respect to a lumen of the catheter can be favorably ensured.

When the catheter is introduced into a blood vessel through a blood vessel of an arm and is inserted into a blood vessel of the lower extremity, a time for pressing the introducing site (incision site) in the blood vessel and a lying-in-bed time after an operation can be shortened because the catheter is introduced through the blood vessel of an arm in which invasiveness is low, The burden to a patient can thus be reduced. In addition, the catheter main body is relatively thin in wall thickness. Thus, a large-sized medical instrument can be inserted into the lumen of the catheter. Therefore, from a viewpoint of reducing a burden to the body of a patient, the catheter is suitable for treatment in which the inner diameter of a blood vessel at a target site is greater than the inner diameter of a blood vessel at an insertion site of the catheter, such as treatment in which the catheter is inserted into a blood vessel of the lower extremity through a blood vessel of an arm.

DETAILED DESCRIPTION

Set forth below is a detailed description of embodiments of a catheter and a method of manufacturing the catheter representing examples of the inventive catheter and method disclosed here. Note that, for the convenience of description, there are cases where the dimensional ratios of the drawings are exaggerated and are different from the actual ratios. In the description below, the hand side or end (i.e., operator side) of the catheter will be referred to as "the proximal side" or "the proximal end", and a side or end to be inserted into a living body will be referred to as "the distal side" or "the distal end".

Figure 1:
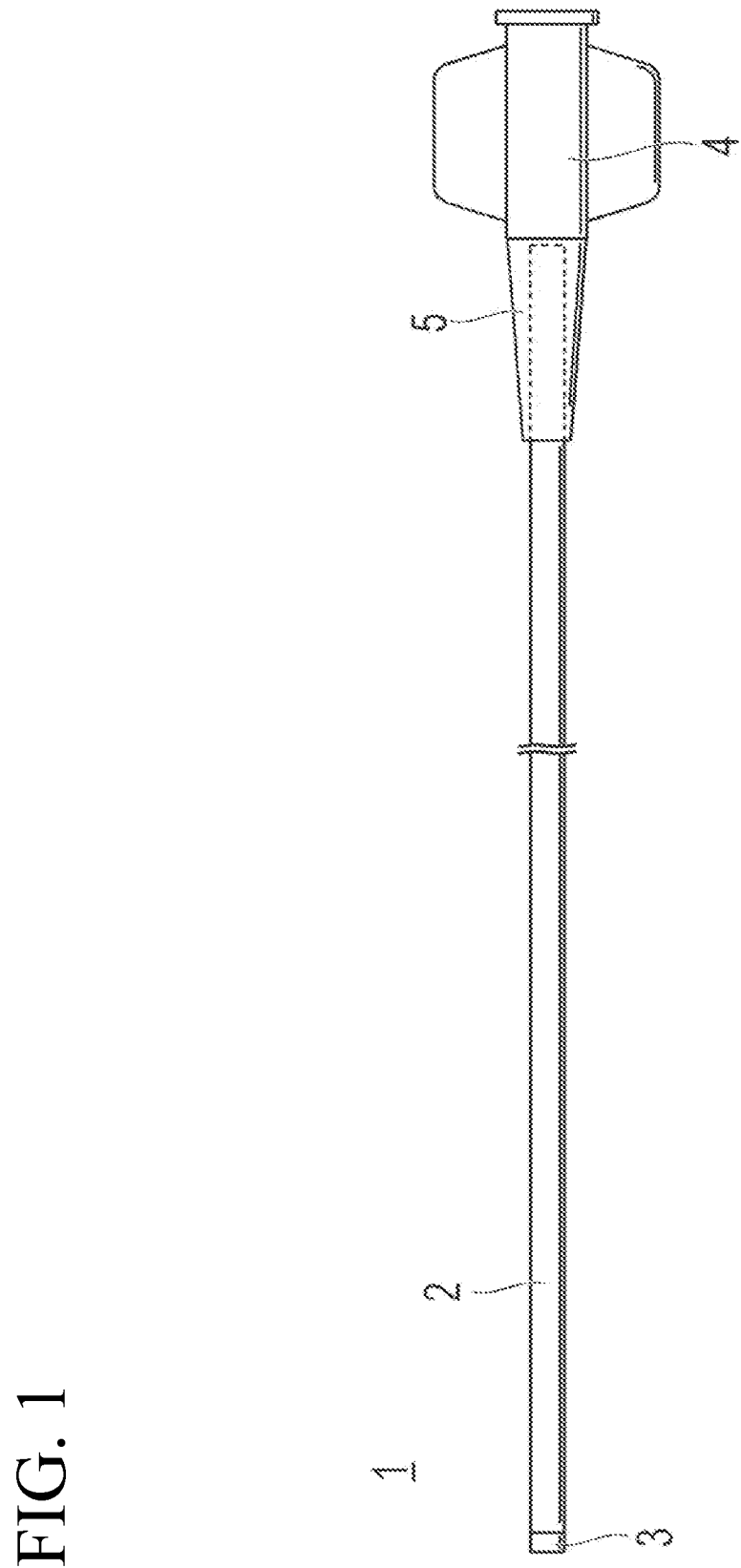
FIG. 1 is a plan view illustrating a catheter of an embodiment.

A catheter 1 illustrated in FIG. 1 is used as a guiding catheter for inducing a treatment catheter (a medical instrument) into a living body. Examples of treatment catheters are a dilation catheter (a balloon catheter) and a catheter through which a stent is transported to a stenosed site (a stent transporting catheter) in a state of being decreased in diameter (contracted), is increased in diameter (expands) at the stenosed site, and is caused to indwell at the stenosed site so as to retain the stenosed site in the expanded state. The guiding catheter and treatment catheter may be introduced, for example, through a blood vessel of an arm such as the radial artery to a target site such as a stenosed site in a blood vessel of the lower extremity.

The catheter 1 includes a catheter main body 2, a flexible soft tip 3 provided on the distal side of the catheter main body 2, a hub 4 provided on the proximal side of the catheter main body 2, a strain relief 5 (a covering member) covering a portion where the catheter main body 2 and the hub 4 are joined.

Figure 2:
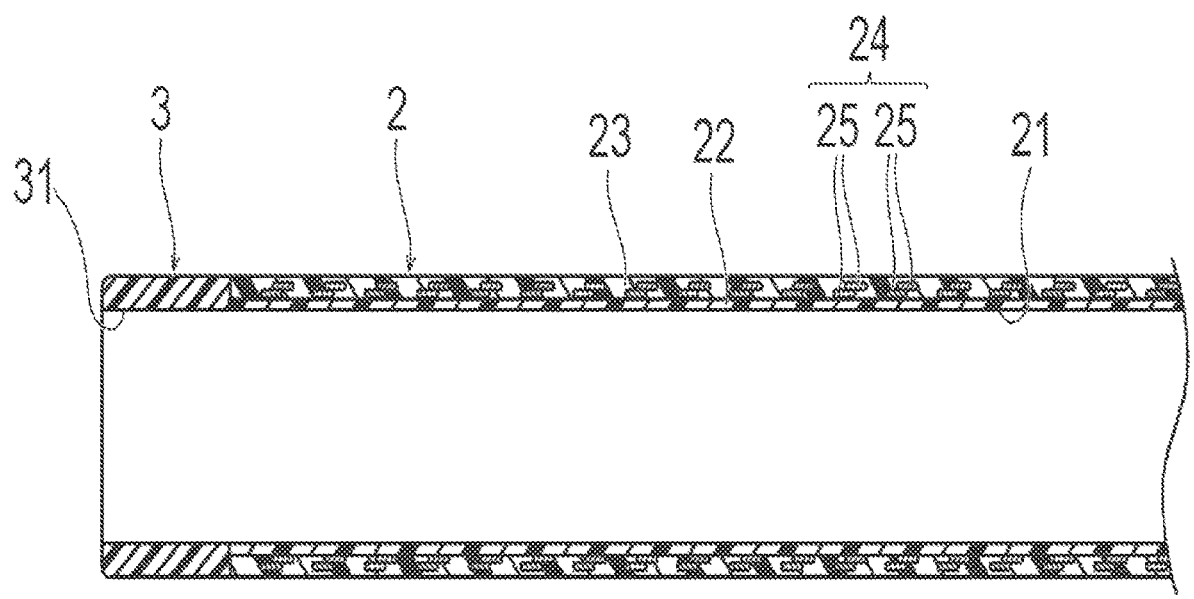
FIG. 2 is a longitudinal cross-sectional view illustrating the catheter of the embodiment.
Figure 3:
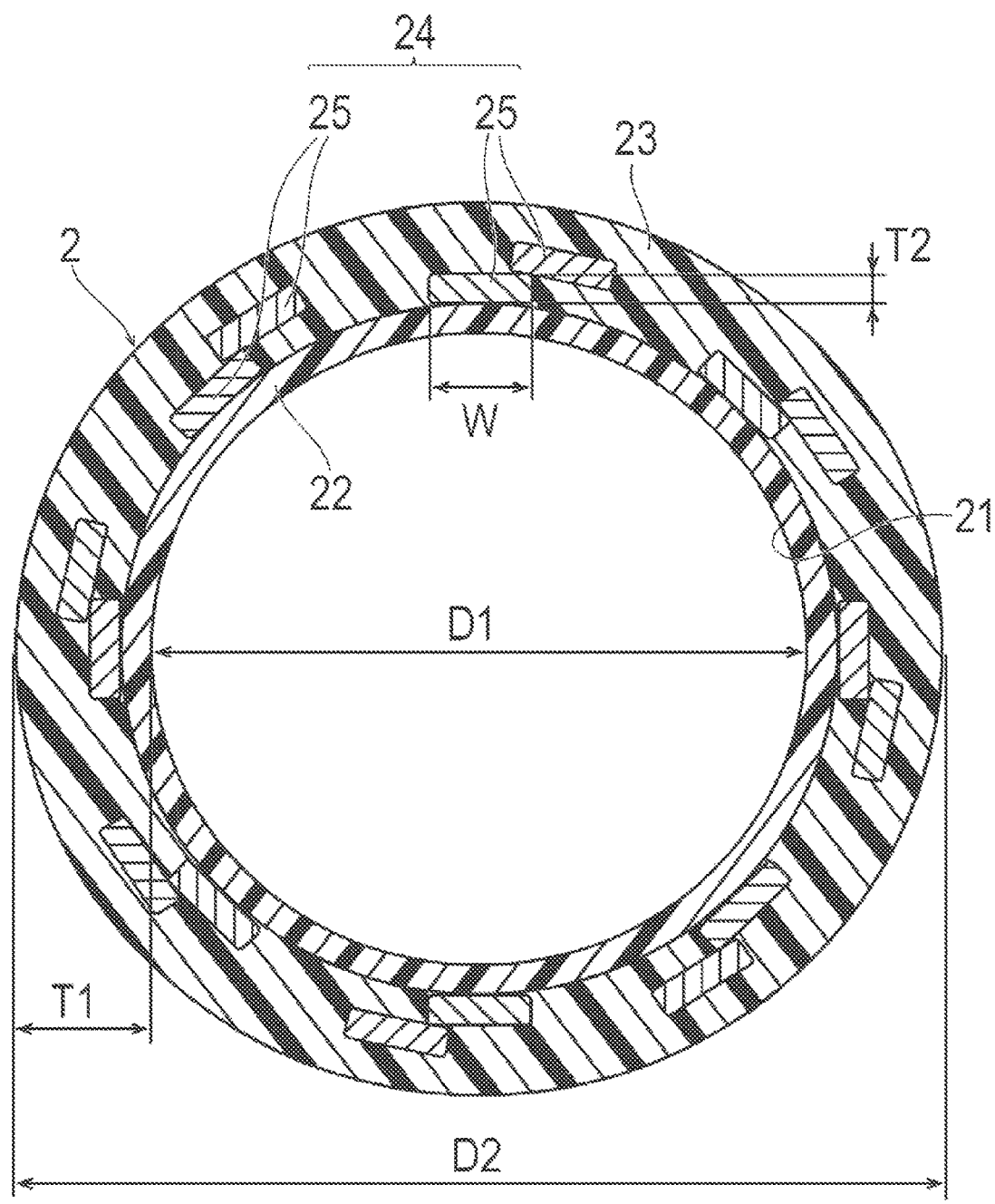
FIG. 3 is a transverse cross-sectional view illustrating the catheter of the embodiment.

As illustrated in FIGS. 2 and 3, the catheter main body 2 is an elastic tube-shaped body. A lumen 21 is formed at substantially the center portion (i.e., in the radial direction) throughout the overall length of the catheter main body 2. The lumen 21 is open at a distal opening portion 31 of the distal end of the soft tip 3 (i.e., the interior of the lumen 21 communicates with the exterior of the catheter 1).

The catheter main body 2 includes an inner layer 22 forming the inner surface inside the lumen 21, an outer layer 23 forming the outer surface, and a reinforcement layer 24 positioned between the inner layer 22 and the outer layer 23 (i.e., embedded in the wall of the catheter main body to be located between the inner surface of the catheter main body 2 and the outer surface of the catheter main body 2).

Examples of materials of the outer layer 23 include various types of thermoplastic elastomers or the like such as a styrene-based elastomer, a polyolefin-based elastomer, a polyurethane-based elastomer, a polyester-based elastomer, a polyimide-based elastomer, a polybutadiene-based elastomer, a trans-polyisoprene-based elastomer, a fluororubber-based elastomer, and a chlorinated polyethylene-based elastomer. One type or a combination of two or more types of these materials (a polymer alloy, a polymer blend, a laminated body, and the like) can be used.

The inner layer 22 is preferably made of a material which has low friction when contacting at least a portion of a medical instrument (such as a treatment catheter and a guide wire (not illustrated)) when the medical instrument is inserted into the lumen 21. Accordingly, a medical instrument inserted into the catheter main body 2 can be moved in the axial line direction against smaller sliding friction (i.e., relatively low friction), thereby improving operability. Naturally, the inner layer 22 in its entirety may be formed of a low-friction material. Examples of a low-friction material include a fluorine-based resin material such as polytetrafluoroethylene (PTFE).

Figure 4:
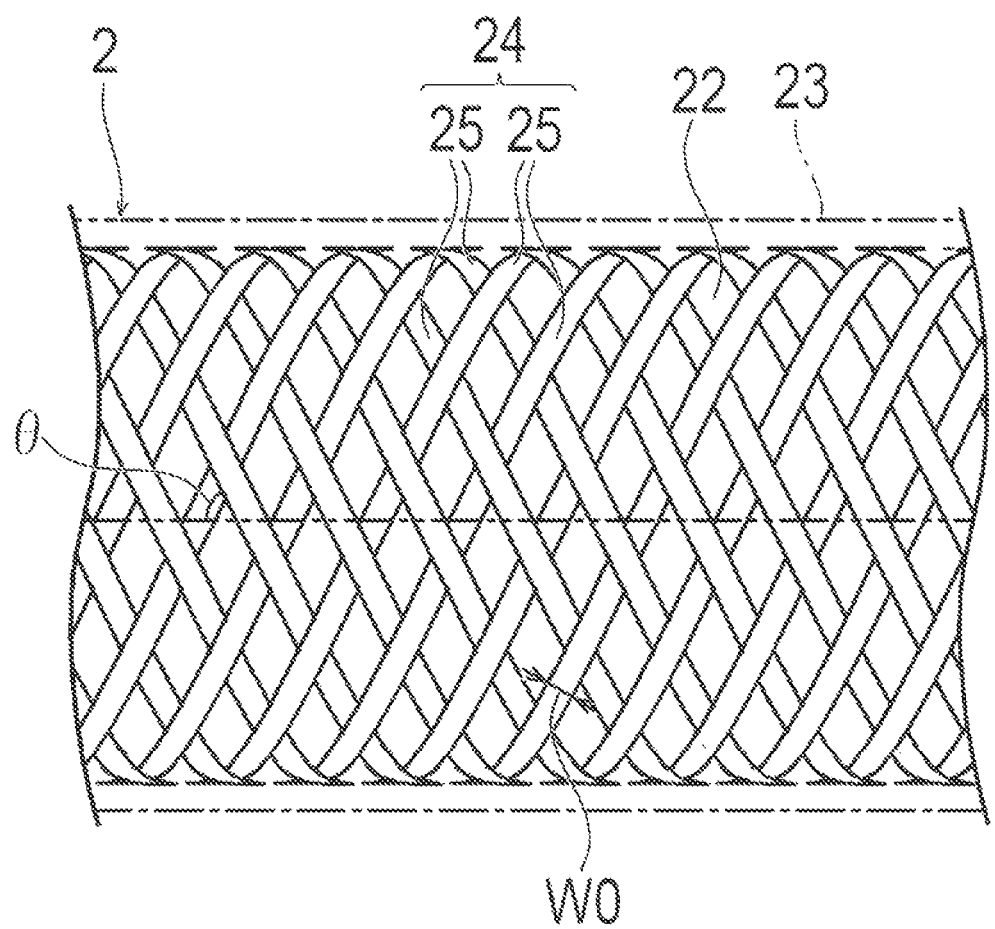
FIG. 4 is a perspective view observing reinforcements which are shown through an outer layer of the catheter of the embodiment.

The reinforcement layer 24 reinforces the catheter main body 2. As illustrated in FIGS. 2 to 4, the reinforcement layer 24 includes multiple reinforcements 25 (e.g., filaments, wires or strands). Gaps between the multiple reinforcements 25 in the reinforcement layer 24 are configured to allow a resin of the outer layer 23 or the inner layer 22 to enter. In the present embodiment, multiple reinforcements 25 are wound around (i.e., helically-wound around) on the outer surface of the inner layer 22. Examples of the material of the reinforcement layer 24 include spiral or meshed reinforcements 25. Each reinforcement 25 is configured to be metal, such as stainless steel, Ni—Ti alloy. One specific example of a reinforcement 25 is a flat plate-shaped reinforcement 25 obtained by squeezing a stainless steel wire so as to have a flat plate shape, which allows the catheter main body 2 to become thin in wall thickness in a radial direction. The reinforcement 25 may also be a material which is spiraled or braided (i.e., a braid body) by using multiple reinforcements ranging in number approximately from 8 to 32. It is preferable that the number of the reinforcements 25 is a multiple of 8 in order to achieve favorably balanced reinforcing in a tubular manner. Note that, the reinforcement 25 is not limited to the above-described flat plate-shaped wire material. For example, the reinforcement 25 may be a round or elliptical wire material (i.e., a wire material with a round or elliptical transverse cross-section). In addition, one reinforcement 25 may be formed of a bundle including two or more reinforcements.

According to such a reinforcement layer 24, sufficient rigidity and strength can be ensured without causing the catheter main body 2 to be increased in wall-thickness. In other words, sufficient rigidity and strength can exist even though the inner diameter of the catheter main body 2 is relatively increased. As a result, a medical instrument having a relatively significant (i.e., large) outer diameter can be inserted into the lumen 21 of the catheter main body 2, and it is possible to obtain a catheter 1 which excels in pushability and torque transmission and in which a kink or squashing is unlikely to occur.

When the reinforcement 25 has a flat plate shape, it is preferable that the shape of a cross section orthogonal to the longitudinal direction is substantially rectangular. It is also preferable when the reinforcement 25 is flat-plate shaped that the side along the circumferential direction of the catheter main body 2 becomes the long side, and the side along the radial direction of the catheter main body 2 becomes the short side (i.e., the side in the radial direction is shorter than the side in the circumferential direction). Here, a width WO of the reinforcement 25 is the length of the long side, and a thickness T2 of the reinforcement 25 is the length of the short side. A cross-sectional shape of the reinforcement 25 is thus substantially rectangular. However, another cross-sectional shape of the reinforcement 25 is acceptable as long as the width direction of the reinforcement 25 is substantially straight. The thickness may be differently formed depending on a position in the width direction. Since the flat plate-shaped reinforcement 25 uniformly receives force with respect to external stress compared to a reinforcement 25 having an elliptical shape, physical properties become steady (i.e., more uniform).

Therefore, it is suitable (i.e., beneficial) that the reinforcement 25 is a flat plate-shaped wire material.

The pitch of the reinforcements 25 (i.e., the length of the catheter main body 2 in the axial line direction when the same reinforcement 25 is spirally wound around once (360 degrees)) preferably ranges from 1.5 to 7 mm, and more preferably ranges from 2 to 5 mm. However, the pitch is not limited to these values. The pitch of the reinforcements 25 may be differently formed depending on a position in the axial line direction of the catheter main body 2.

An angle θ of each reinforcement 25 with respect to the axial line direction of the catheter main body 2 preferably ranges from 10 degrees to 80 degrees, and more preferably ranges from 45 degrees to 75 degrees. However, the angle θ is not limited thereto. The angle θ may be different depending on a position in the long-axis direction of the catheter main body 2.

Since the reinforcement 25 is obliquely wound with respect to the axial line direction of the catheter main body 2, an effective width W of the reinforcement 25 on a cross section orthogonal to the axial line direction of the catheter main body 2 is greater than the width WO of each reinforcement 25. The effective width W of the reinforcement 25 is a width which is practically applied (i.e., the equivalent force that would be applied by a reinforcement 25 having the effective width) with respect to a curve or a kink of the catheter main body 2.

The number of layers configuring/forming the catheter main body 2, the configuration material of each layer, the presence or absence of the reinforcement 25, and the like may be differently formed along the longitudinal direction of the catheter main body 2. For example, a portion of the catheter main body 2 on the distal side can have a reduced number of layers, utilize a more flexible material, or can omit (i.e., not have) the reinforcement layer 24 in only the portion in order to enhance flexibility in this portion of the catheter main body 2 (e.g., at the distal end).

The catheter 1 is inserted into a human body while the position of the catheter 1 is checked under a radioscopic condition. Therefore, it is preferable that a radiopaque material (an X-ray contrast agent) is compounded in the configuration material of the outer layer 23. Examples of radiopaque materials include barium sulfate, bismuth oxide, tungsten, and the like. Moreover, the compound ratio of the radiopaque material to the configuration material of the outer layer 23 preferably ranges from 30 to 80 wt %.

In addition, such a radiopaque material is not limited to being present throughout the overall length of the catheter main body 2. The radiopaque material may be partially present in the catheter main body 2, for example, in only a distal portion or only the soft tip 3.

At least a portion of the catheter main body 2 may be curved. Due to the curved shape, the catheter main body 2 can have a shape suitable for an insertion site in accordance with the purpose of the catheter 1 or can easily engage with a target site.

The soft tip 3 illustrated in FIGS. 1 and 2 is configured to be formed of a flexible material. The distal end of the soft tip 3 preferably has a rounded shaped. Providing a soft tip 3 of this nature allows traveling/movement within the body to be performed smoothly and safely even inside curved, meandering, and bifurcated blood vessels. Examples of materials for the soft tip 3 include various types of rubber materials such as natural rubber, isoprene rubber, butadiene rubber, chloroprene rubber, silicone rubber, fluorine rubber, and styrene-butadiene rubber; and various types of thermoplastic elastomers such as a styrene-based elastomer, a polyolefin-based elastomer, a polyurethane-based elastomer, a polyester-based elastomer, a polyimide-based elastomer, a polybutadiene-based elastomer, a trans-polyisoprene-based elastomer, a fluororubber-based elastomer, and a chlorinated polyethylene-based elastomer.

The length of the soft tip 3 is not particularly limited. Generally, the length of the soft tip 3 preferably ranges from approximately 0.5 to 3 mm, and more preferably ranges from approximately 1 to 2 mm.

The hub 4 is mounted in the proximal end of the catheter main body 2 as illustrated in FIG. 1. A passage communicating with the lumen 21 is formed in the hub 4. The passage has an inner diameter substantially equal to the inner diameter of the lumen 21 and leads to the inner surface of a proximal portion of the lumen 21 while generating no step or the like (i.e., the inner surface of the proximal portion of the lumen 21 is flush/even with the inner walls of the passage).

Examples of medical devices/instruments that may be inserted through the hub 4 include an elongated body (a wire-like body) such as a guide wire, catheters (for example, a PTCA balloon catheter, and a stent transporting catheter), an endoscope, an ultrasonic probe, and a temperature sensor is inserted or evulsed, and various types of liquid such as a contrast agent (an X-ray contrast agent), a drug solution, and a physiological saline solution can be injected. In addition, for example, the hub 4 can also be connected to a different instrument such as a bifurcated Y-type connector.

The strain relief 5, which is illustrated in FIG. 1, is formed of an elastic material. The strain relief 5 covers a portion where the catheter main body 2 and the hub 4 are joined to each other, thereby playing a role of preventing bending (a kink) in the vicinity of the portion.

Desirable conditions for the dimensions of each portion of the catheter main body 2 according to the present embodiment are described below.

An outer diameter D2 of the catheter main body 2 preferably ranges from 2 mm to 3 mm. If the outer diameter D2 is excessively significant (i.e., too large), operability at the time of inserting the catheter main body 2 into a blood vessel such as the radial artery and operability when moving the catheter main body 2 within the living body deteriorates. Moreover, there is concern that a burden to a patient (e.g., potential harm within the living body) increases. In addition, the effective width W of the reinforcement 25 preferably ranges from 0.200 mm to 0.600 mm (i.e., is at least 0.200 mm and not greater than 0.600 mm). If the effective width W is excessively small, kink resistance of the catheter main body 2 deteriorates because the catheter main body 2 is insufficiently reinforced (i.e., it is too flexible) in the circumferential direction of the outer diameter D2. In addition, if the effective width W is excessively significant (i.e., too large), flexibility of the catheter main body 2 deteriorates (i.e., the catheter main body 2 is overly rigid), and thus, kink resistance of the catheter main body 2 deteriorates. In order to sufficiently help ensure reinforcing in the circumferential direction of the outer diameter D2 performed by one reinforcement 25 in a cross section of the catheter main body 2, the effective width W of the reinforcement 25 more preferably ranges from 0.300 mm to 0.500 mm (i.e., is at least 0.300 mm and not greater than 0.500 mm).

In the catheter 1, when the wall thickness of the catheter main body 2 is T1, the thickness of each reinforcement 25 is T2, the inner diameter of the catheter main body 2 is D1, the outer diameter of the catheter main body 2 is D2, the effective width of each reinforcement 25 is W, and the number of the reinforcements 25 is N, it is preferable that Expressions (1), (2), and (3) below are satisfied.

$$0.050 \text{ mm} \leq T1 \leq 0.100 \text{ mm} \quad \text{Expression (1)}$$

$$T2/T1 \geq 0.25 \quad \text{Expression (2)}$$

$$60{,}000 \leq (D1 \times D2 \times W \times N)/(T1^2 \times T2) < 1{,}000{,}000 \quad \text{Expression (3)}$$

The wall thickness T1 of the catheter main body 2 in Expression (1) denotes that the thickness of the catheter main body in the radial direction (the wall thickness direction) of the catheter main body 2 ranges from 0.050 mm to 0.100 mm.

In Expression (2), a value A (=T2/T1) is the ratio of the thickness T2 of the reinforcement 25 to the wall thickness T1 of the catheter main body 2. This value A indicates the degree of reinforcing in the radial direction (the wall thickness direction) performed by the reinforcement 25. When the value A is equal to or greater than 0.25, and the reinforcements 25 overlap each other due to the braided state, the value A denotes that the thickness of the overlapping portion occupied by two reinforcements 25 becomes equal to or greater than half the wall thickness T1 of the catheter main body 2.

When a value of the second term (the central term—i.e., $(D1 \times D2 \times W \times N)/(T1^2 \times T2)$) in Expression (3) is B, in a case where a value B1 and a value B2 are defined as shown in Expressions (4) and (5), the value B can be expressed through Expression (6).

$$B1 = (D1/T1) \times (D2/T1) \quad \text{Expression (4)}$$

$$B2 = (W \times N)/T2 \quad \text{Expression (5)}$$

$$B = B1 \times B2 \quad \text{Expression (6)}$$

First, Expression (4) will be described. Generally, a kink of the catheter main body 2 is likely to occur as the diameter increases and is likely to occur as the wall thickness decreases. Therefore, the value B1 (which is the product of the values respectively obtained by dividing the inner diameter D1 and the outer diameter D2 of the catheter main body 2 by the wall thickness T1) can be an index expressing how unlikely it is that a kink occurs (kink resistance).

Hoop stress generated on the inner surface of a circular tube in the circumferential direction when internal pressure is applied inside the circular tube is expressed by an equation of (internal pressure×(inner diameter/wall thickness)). The circular tube is likely to deform as the hoop stress increases. Here, when the internal pressure of the catheter main body 2 is considered to be steady (i.e., constant), a value of (inner diameter/wall thickness) indicates how easily the catheter main body 2 deforms. It is possible to predict that a kink is likely to occur as the value of (inner diameter D1/wall thickness T1) of the catheter main body 2 increases. Note that, hoop stress is stress applied to the inner surface of the circular tube. However, the catheter main body 2 according to the present embodiment is characterized by being thin in wall thickness, and the difference between the inner diameter D1 and the outer diameter D2 is not so significant (i.e., the difference between the inner diameter D1 and the outer diameter D2 is relatively small). Accordingly, the hoop stress can also be an index similarly for the value of (outer diameter D2/wall thickness T1).

Figure 5:
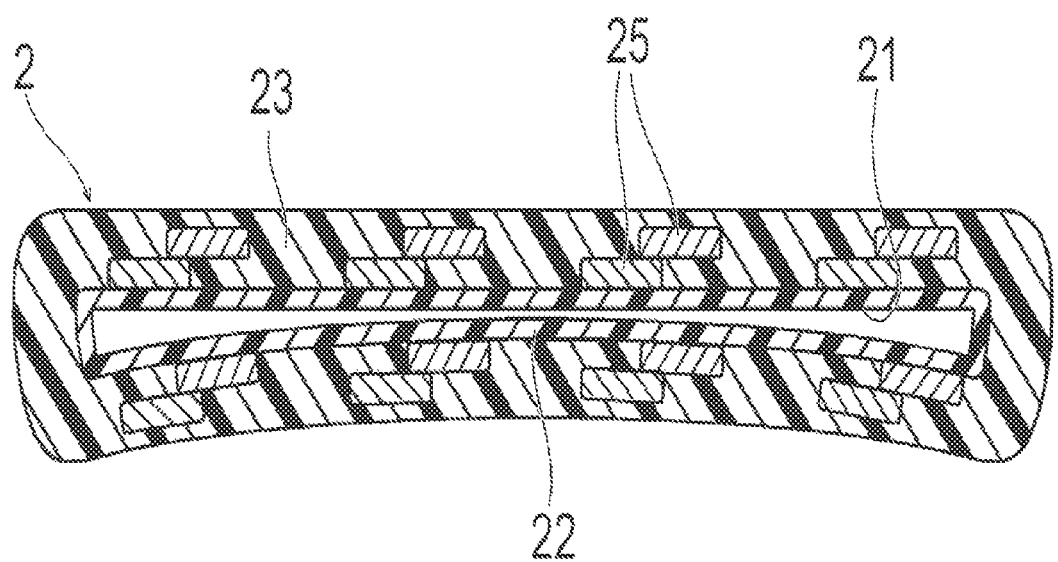
FIG. 5 is a transverse cross-sectional view illustrating a state where the catheter of the embodiment is kinked.

When the catheter main body 2 is caused to meander so as to be kinked (i.e., possess a kinked portion), as illustrated in FIG. 5, a portion on a side having a convex shape in the meandering state (upper side of FIG. 5) exhibits a substantially straight shape in a cross section (i.e., the cross-section is substantially straight/linear). Since the portion is pushed by the squashed/deformed catheter main body 2, it is difficult to widen the portions. In contrast, a portion on a side having a concave shape in the meandering state (lower side FIG. 5) exhibits an arc shape in the cross section, and the portion is more easily widened compared to the substantially straight portion. In addition, as shown in FIG. 5, when the outer diameter D2 increases, the radius of curvature increases. Therefore, the portion is more easily widened. Moreover, when the catheter main body 2 has a relatively small wall thickness T1, a kinked portion is naturally more easily widened. Therefore, how easily a kinked portion is widened can be expressed through the equation of D2/T1.

Expression (5) will be described next. The value B2 is obtained by multiplying the effective width W of the reinforcement 25 and the number N of the reinforcements 25 and dividing the product by the thickness T2 of the reinforcement 25. The total length of the N reinforcements 25 in the circumferential direction (the width direction) in a cross section of the catheter main body 2 is calculated by multiplying the effective width W of the reinforcement 25 and the number N of the reinforcements 25. The influence of the thickness T2 is eliminated by dividing the calculated value by the thickness T2 of the reinforcement 25. In other words, the relationship between the wall thickness T1 of the catheter main body 2 and the thickness T2 of the reinforcement 25 is defined by Expression (2). Therefore, in Expression (5) included in Expression (3), the influence of the thickness T2 of the reinforcement 25 is eliminated (i.e., removed). When the total length of the reinforcements 25 in the width direction is significant (i.e., relatively large), it is considered that a kink is unlikely to occur. Therefore, the value B2 can be an index expressing kink resistance.

As described above, the value B1 of Expression (4) is an index focused on the stress generated in the catheter main body 2, and the value B2 of Expression (5) is an index focused on the strength of the reinforcements 25 in the circumferential direction. Therefore, the value B obtained by multiplying the value B1 and the value B2 becomes an index expressing kink resistance of the catheter main body 2 and maneuverability of a medical instrument in the lumen 21 of the catheter main body 2 when the catheter main body 2 is kinked. Note that, "maneuverability of a medical instrument in the lumen 21 of the catheter main body 2 when the catheter main body 2 is kinked" denotes the properties/ability of a medical instrument to relatively easily pass through the lumen 21 of the kinked catheter main body 2 when the catheter main body 2 is kinked. Here, as the value B increases, rigidity related to the wall thickness T1 of the catheter main body 2 deteriorates (i.e., the catheter main body 2 becomes less rigid). Accordingly, the catheter main body 2 is more likely to be kinked, and the medical instrument more easily passes therethrough when the catheter main body 2 is kinked. Therefore, if the value B is less than 60,000, it is difficult for the medical instrument to be inserted when a kink occurs. If the value B exceeds 1,000,000, the wall thickness T1 of the catheter main body 2 becomes excessively thin. When the value B exceeds 1,000,000 there is thus a concern that the reinforcements 25 may stick out from the catheter main body 2 leading to a phenomenon such as damage to a living body. From the viewpoint of enhancing the rigidity of the catheter main body 2 and also enhancing the kink resistance, it is more preferable that the value B ranges from 80,000 to less than 500,000.

When the value A is equal to or greater than 0.25 as shown in Expression (2), the reinforcements 25 are able to reinforce (i.e., provide sufficient rigidity) the catheter main body 2 in the radial direction. When the value B ranges from 60,000 to less than 1,000,000 as shown in Expression (3), the shape of the catheter main body 2 is defined to be a shape unlikely to be kinked due to the value B1 included in the value B. Additionally, when the value B ranges from 60,000 to less than 1,000,000 as shown in Expression (3), reinforcing in the circumferential direction (the width direction) performed by all of the N reinforcements 25 is ensured due to the value B2 included in the value B. Therefore, the significant inner diameter D1 of the catheter main body 2 can be ensured relative to the outer diameter D2 (i.e., a relatively large inner diameter is provided). In addition, even in a case where the catheter main body 2 is kinked, a medical instrument can pass through the lumen 21 of the catheter main body 2 because a certain clearance is provided in the lumen 21. Moreover, the lumen 21 which becomes narrow due to a kink occurring when a medical instrument is thrust can be widened, and the medical instrument can pass therethrough. Thus, maneuverability of a medical instrument can be favorably ensured.

The catheter 1 does thus not possess a catheter main body 2 which does not kink at all. Instead, the catheter main body 2 allows a kink to a certain extent/degree and allows a medical instrument to pass through the kinked portion even in a case of being kinked.

In other words, in a guiding catheter in the related art that is significant in inner and outer diameters (7 Fr to 10 Fr), the catheter main body has a significant wall thickness and the reinforcement has a significant thickness in order to help ensure pressure resistance and kink resistance. According to this configuration, the catheter main body becomes unlikely to be squashed (i.e., deformed), and the lumen is ensured (i.e., the lumen maintains its shape). In contrast, the catheter 1 according to the present embodiment exhibits an operation effect different from that in the related art because maneuverability of a medical instrument with respect to a kinked portion may be recovered/enabled by the guide wire widening the lumen 21 of the catheter main body 2. From the viewpoint of making the catheter main body 2 thin in wall thickness, in the catheter 1 according to the present embodiment, the thickness of each reinforcement 25 is preferably equal to or less than 0.035 mm.

In addition, the value B more preferably ranges from 80,000 to less than 500,000. When the value B ranges from 80,000 to less than 500,000, the catheter main body 2 has suitable hardness which is not excessively flexible, maneuverability of a medical instrument with respect to a kinked portion is favorably ensured, and pushability and torque transmission of the catheter main body 2 inside a biological lumen are also favorably ensured. Thus, overall operability is improved.

In addition, the value B more preferably ranges from 85,000 to less than 250,000. When the value B ranges from 85,000 to less than 250,000, the catheter main body 2 has more suitable hardness, maneuverability of a medical instrument with respect to a kinked portion is favorably ensured, and pushability and torque transmission of the catheter main body 2 inside a biological lumen become excellent. Thus, overall operability is further improved.

In addition, the catheter main body 2 can be inserted into a thin biological lumen and a burden to a patient can be reduced because the outer diameter D2 of the catheter main body 2 ranges from 2 mm to 3 mm (i.e., is at least 2 mm and not greater than 3 mm).

In addition, as illustrated in a maneuverability evaluation test described below, when the catheter main body 2 is bent 180° and a kinked portion is made (i.e., the catheter main body 2 possesses a kinked portion), in a cross-sectional shape of the kinked portion of the catheter main body at the time an angle formed by the kinked portion returns to 90°, it is preferable that spaces formed at a left end and a right end of the lumen 21 of the catheter main body 2 (i.e., areas that are outward in the radial direction) are greater than a space formed at the center of the left end and the right end of the lumen 21 of the catheter main body 2 (i.e., the area between the radial outer ends). In this configuration, when the catheter 1 is delivered to a target site inside a biological lumen, even though the catheter 1 is kinked, the guide wire can pass through the lumen 21 of the catheter 1 on the distal side closer than the kinked portion via the clearances formed at the left end and the right end of the lumen at the kinked portion of the catheter 1. Therefore, a medical instrument can be inserted into the lumen 21 of the catheter 1 by utilizing the guide wire. Accordingly, there is no need for an operator to replace the catheter 1 even though the catheter 1 is kinked. The treatment time of an operator is thus shortened, and a burden to the body of a patient can be reduced.

As illustrated in the maneuverability evaluation test described below, when the catheter main body 2 is bent 180° and a kinked portion is made, it is preferable that the lumen 21 of the kinked portion of the catheter main body 2 at the time an angle formed by the kinked portion returns to 90° allows a guide wire having an outer diameter of 0.89 mm to be inserted through the kinked portion of the lumen 21. In this configuration, when the catheter 1 is delivered to a target site inside a biological lumen, a medical instrument such as the guide wire can be inserted into the lumen 21 of the catheter 1 even though the catheter 1 is kinked. The catheter 1 thus does not need to be replaced. Therefore, a treatment time of an operator is shortened, and a burden to the body of a patient can be reduced.

As further illustrated by the kink resistance evaluation test described below, it is preferable that the distance between a turned-back end of a loop and a plate is configured to be equal to or less than 45 mm at the time the loop is made by causing the catheter main body 2 to pass through two penetration holes that are parallel to each other. The two penetration holes preferably have diameters of 2.8 mm and are open at portions of the plate where the center-to-center distance is 10 mm. The plate preferably has a thickness of 10 mm in water of 37° C. and a kink occurs by pulling one end of the catheter main body 2. In this configuration, kink resistance of the catheter 1 is enhanced. Even in a case where the catheter 1 is kinked, maneuverability of a medical instrument with respect to the lumen 21 of the catheter 1 can be favorably ensured.

When the catheter 1 is introduced into a blood vessel through a blood vessel such as the radial artery of an arm and is inserted into a blood vessel of the lower extremity, the time for pressing the introducing site (incision site) in the blood vessel and a lying-in-bed time after an operation can be reduced because the catheter main body 2 is introduced through the blood vessel of an arm in which invasiveness is low. The burden to a patient can thus be reduced. In addition, in the catheter 1 according to the present embodiment, the catheter main body 2 is thin in wall thickness. A relatively large-sized medical instrument can thus be inserted into the lumen 21 of the catheter 1. Therefore, from a viewpoint of reducing the burden to a patient's body, the catheter is suitable for treatment in which the inner diameter of a blood vessel at a target site is greater than the inner diameter of a blood vessel at an insertion site of the catheter 1, such as treatment in which the catheter is inserted into a blood vessel of the lower extremity through a blood vessel of an arm.

Examples of the catheter disclosed here are described below.

Example 1

In a wire material in which an inner layer consisting of polytetrafluoroethylene (PTFE) was formed on a copper wire having a diameter of 2.160 mm corresponding to the inner diameter of a prepared catheter, sixteen flat plate-shaped reinforcements consisting of SUS304 were uniformly arranged in the circumferential direction. Each of the reinforcements had a width of 0.080 mm and a thickness of 0.035 mm. Eight of the reinforcements were arranged in the same direction and the remaining eight were arranged in the opposite direction. The reinforcements were braided at pitches of 0.180 mm and were thus helically-wound. The effective width of each reinforcement was 0.272 mm.

Subsequently, both ends of each of the reinforcements were cut. The cut reinforcement was covered with a tube consisting of a polyester elastomer. The entirety of the tube was covered with a heat shrinkable tube and was heated, and the tube was subjected to heat welding as an outer layer with respect to the inner layer. Thereafter, the heat shrinkable tube was stripped and the copper wire was removed, thereby obtaining a pipe body having a lumen and possessing an outer diameter of 2.360 mm, an inner diameter of 2.160 mm, and a thickness of 0.100 mm.

Subsequently, a soft tip was connected to the obtained pipe body and was heated inside a die so as to be rounded. A catheter main body was thus formed. A hub and a strain relief were attached to the proximal side of the completed catheter main body to obtain a catheter.

In the obtained catheter, the value A was 0.350 and the value B was 63,296.

Example 2

A catheter was prepared through the same method as Example 1 except that the width of the reinforcement was set to 0.110 mm, the thickness of the reinforcement was set to 0.030 mm, the pitch of the reinforcements was set to 0.150 mm, the effective width of the reinforcement was set to 0.322 mm, the outer diameter of the catheter main body was set to 2.040 mm, the inner diameter of the catheter main body was set to 1.850 mm, and the wall thickness of the catheter main body was set to 0.095 mm. In the obtained catheter, the value A was 0.316 and the value B was 71,750.

Example 3

A catheter was prepared through the same method as Example 1 except that the width of the reinforcement was set to 0.110 mm, the thickness of the reinforcement was set to 0.030 mm, the pitch of the reinforcements was set to 0.250 mm, the effective width of the reinforcement was set to 0.277 mm, the outer diameter of the catheter main body was set to 2.360 mm, the inner diameter of the catheter main body was set to 2.160 mm, the wall thickness of the catheter main body was set to 0.100 mm. In the obtained catheter, the value A was 0.300 and the value B was 75,377.

Example 4

A catheter was prepared through the same method as Example 1 except that the width of the reinforcement was set to 0.110 mm, the thickness of the reinforcement was set to 0.030 mm, the pitch of the reinforcements was set to 0.250 mm, the effective width of the reinforcement was set to 0.316 mm, the outer diameter of the catheter main body was set to 2.356 mm, the inner diameter of the catheter main body was set to 2.160 mm, and the wall thickness of the catheter main body was set to 0.098 mm. In the obtained catheter, the value A was 0.306 and the value B was 89,302.

Example 5

A catheter was prepared through the same method as Example 1 except that the width of the reinforcement was set to 0.127 mm, the thickness of the reinforcement was set to 0.025 mm, the pitch of the reinforcements was set to 0.250 mm, the effective width of the reinforcement was set to 0.307 mm, the outer diameter of the catheter main body was set to 2.360 mm, the inner diameter of the catheter main body was set to 2.160 mm, and the wall thickness of the catheter main body was set to 0.100 mm. In the obtained catheter, the value A was 0.250 and the value B was 99,998.

Example 6

A catheter was prepared through the same method as Example 1 except that the width of the reinforcement was set to 0.110 mm, the thickness of the reinforcement was set to 0.030 mm, the pitch of the reinforcements was set to 0.150 mm, the effective width of the reinforcement was set to 0.372 mm, the outer diameter of the catheter main body was set to 2.360 mm, the inner diameter of the catheter main body was set to 2.160 mm, and the wall thickness of the catheter main body was set to 0.100 mm. In the obtained catheter, the value A was 0.300 and the value B was 101,031.

Example 7

A catheter was prepared through the same method as Example 1 except that the width of the reinforcement was set to 0.160 mm, the thickness of the reinforcement was set to 0.030 mm, the pitch of the reinforcements was set to 0.150 mm, the effective width of the reinforcement was set to 0.464 mm, the outer diameter of the catheter main body was set to 2.360 mm, the inner diameter of the catheter main body was set to 2.200 mm, and the wall thickness of the catheter main body was set to 0.080 mm. In the obtained catheter, the value A was 0.375 and the value B was 200,547.

Example 8

A catheter was prepared through the same method as Example 1 except that the width of the reinforcement was set to 0.160 mm, the thickness of the reinforcement was set to 0.025 mm, the pitch of the reinforcements was set to 0.200 mm, the effective width of the reinforcement was set to 0.406 mm, the outer diameter of the catheter main body was set to 2.350 mm, the inner diameter of the catheter main body was set to 2.200 mm, and the wall thickness of the catheter main body was set to 0.075 mm. In the obtained catheter, the value A was 0.333 and the value B was 238,553.

Example 9

A catheter was prepared through the same method as Example 1 except that the width of the reinforcement was set to 0.200 mm, the thickness of the reinforcement was set to 0.020 mm, the pitch of the reinforcements was set to 0.150 mm, the effective width of the reinforcement was set to 0.528 mm, the outer diameter of the catheter main body was set to 2.393 mm, the inner diameter of the catheter main body was set to 2.260 mm, and the wall thickness of the catheter main body was set to 0.067 mm. In the obtained catheter, the value A was 0.301 and the value B was 516,794.

Example 10

A catheter was prepared through the same method as Example 1 except that the width of the reinforcement was set to 0.210 mm, the thickness of the reinforcement was set to 0.015 mm, the pitch of the reinforcements was set to 0.200 mm, the effective width of the reinforcement was set to 0.470 mm, the outer diameter of the catheter main body was set to 2.320 mm, the inner diameter of the catheter main body was set to 2.200 mm, and the wall thickness of the catheter main body was set to 0.060 mm. In the obtained catheter, the value A was 0.250 and the value B was 711,436.

Example 11

A catheter was prepared through the same method as Example 1 except that the width of the reinforcement was set to 0.250 mm, the thickness of the reinforcement was set to 0.015 mm, the pitch of the reinforcements was set to 0.200 mm, the effective width of the reinforcement was set to 0.523 mm, the outer diameter of the catheter main body was set to 2.360 mm, the inner diameter of the catheter main body was set to 2.250 mm, and the wall thickness of the catheter main body was set to 0.055 mm. In the obtained catheter, the value A was 0.273 and the value B was 979,726.

Comparative Example 1

A catheter was prepared through the same method as Example 1 except that the width of the reinforcement was set to 0.100 mm, the thickness of the reinforcement was set to 0.025 mm, the pitch of the reinforcements was set to 2.000 mm, the effective width of the reinforcement was set to 0.107 mm, the outer diameter of the catheter main body was set to 2.360 mm, the inner diameter of the catheter main body was set to 2.200 mm, and the wall thickness of the catheter main body was set to 0.080 mm. In the obtained catheter, the value A was 0.313 and the value B was 55,582.

Comparative Example 2

A catheter was prepared through the same method as Example 1 except that the width of the reinforcement was set to 0.060 mm, the thickness of the reinforcement was set to 0.015 mm, the pitch of the reinforcements was set to 2.000 mm, the effective width of the reinforcement was set to 0.065 mm, the outer diameter of the catheter main body was set to 2.360 mm, the inner diameter of the catheter main body was set to 2.200 mm, and the wall thickness of the catheter main body was set to 0.080 mm. In the obtained catheter, the value A was 0.188 and the value B was 55,984.

Comparative Example 3

A catheter was prepared through the same method as Example 1 except that the width of the reinforcement was set to 0.060 mm, the thickness of the reinforcement was set to 0.025 mm, the pitch of the reinforcements was set to 0.500 mm, the effective width of the reinforcement was set to 0.109 mm, the outer diameter of the catheter main body was set to 2.360 mm, the inner diameter of the catheter main body was set to 2.200 mm, and the wall thickness of the catheter main body was set to 0.080 mm. In the obtained catheter, the value A was 0.313 and the value B was 56,783.

Comparative Example 4

A catheter was prepared through the same method as Example 1 except that the width of the reinforcement was set to 0.060 mm, the thickness of the reinforcement was set to 0.020 mm, the pitch of the reinforcements was set to 0.200 mm, the effective width of the reinforcement was set to 0.208 mm, the outer diameter of the catheter main body was set to 2.450 mm, the inner diameter of the catheter main body was set to 2.200 mm, and the wall thickness of the catheter main body was set to 0.125 mm. In the obtained catheter, the value A was 0.160 and the value B was 57,370.

Comparative Example 5

A catheter was prepared through the same method as Example 1 except that the width of the reinforcement was set to 0.210 mm, the thickness of the reinforcement was set to 0.030 mm, the pitch of the reinforcements was set to 0.200 mm, the effective width of the reinforcement was set to 0.470 mm, the outer diameter of the catheter main body was set to 2.510 mm, the inner diameter of the catheter main body was set to 2.200 mm, and the wall thickness of the catheter main body was set to 0.155 mm. In the obtained catheter, the value A was 0.194 and the value B was 57,667.

Comparative Example 6

A catheter was prepared through the same method as Example 1 except that the width of the reinforcement was set to 0.100 mm, the thickness of the reinforcement was set to 0.020 mm, the pitch of the reinforcements was set to 0.200 mm, the effective width of the reinforcement was set to 0.302 mm, the outer diameter of the catheter main body was set to 2.500 mm, the inner diameter of the catheter main body was set to 2.200 mm, and the wall thickness of the catheter main body was set to 0.150 mm. In the obtained catheter, the value A was 0.133 and the value B was 59,022.

Comparative Example 7

A catheter was prepared through the same method as Example 1 except that the width of the reinforcement was set to 0.210 mm, the thickness of the reinforcement was set to 0.015 mm, the pitch of the reinforcements was set to 0.200 mm, the effective width of the reinforcement was set to 0.470 mm, the outer diameter of the catheter main body was set to 2.300 mm, the inner diameter of the catheter main body was set to 2.200 mm, and the wall thickness of the catheter main body was set to 0.050 mm. In the obtained catheter, the value A was 0.300 and the value B was 1,015,636.

Comparative Example 8

A catheter was prepared through the same method as Example 1 except that the width of the reinforcement was set to 0.250 mm, the thickness of the reinforcement was set to 0.015 mm, the pitch of the reinforcements was set to 0.20 mm, the effective width of the reinforcement was set to 0.525 mm, the outer diameter of the catheter main body was set to 2.360 mm, the inner diameter of the catheter main body was set to 2.26 mm, and the wall thickness of the catheter main body was set to 0.050 mm. In the obtained catheter, the value A was 0.300 and the value B was 1,195,413.

Table 1 shows the conditions of the above-referenced Examples and Comparative Examples.

TABLE 1

| | Outer diameter D2 of catheter (mm) | Inner diameter D1 of catheter (mm) | Wall thickness T1 of catheter (mm) | Width W0 of reinforcement (mm) | Effective width W of reinforcement (mm) | Thickness T2 of reinforcement (mm) | Number of reinforcements | Pitch of reinforcements (mm) | A | B |
|---|---|---|---|---|---|---|---|---|---|---|
| Comparative Example 1 | 2.360 | 2.200 | 0.080 | 0.100 | 0.107 | 0.025 | 16 | 2.000 | 0.313 | 55,582 |
| Comparative Example 2 | 2.360 | 2.200 | 0.080 | 0.060 | 0.065 | 0.015 | 16 | 2.000 | 0.188 | 55,984 |
| Comparative Example 3 | 2.360 | 2.200 | 0.080 | 0.060 | 0.109 | 0.025 | 16 | 0.500 | 0.313 | 56,783 |
| Comparative Example 4 | 2.450 | 2.200 | 0.125 | 0.060 | 0.208 | 0.020 | 16 | 0.200 | 0.160 | 57,370 |
| Comparative Example 5 | 2.510 | 2.200 | 0.155 | 0.210 | 0.470 | 0.030 | 16 | 0.200 | 0.194 | 57,667 |
| Comparative Example 6 | 2.500 | 2.200 | 0.150 | 0.100 | 0.302 | 0.020 | 16 | 0.200 | 0.133 | 59,022 |
| Example 1 | 2.360 | 2.160 | 0.100 | 0.080 | 0.272 | 0.035 | 16 | 0.180 | 0.350 | 63,296 |
| Example 2 | 2.040 | 1.850 | 0.095 | 0.110 | 0.322 | 0.030 | 16 | 0.150 | 0.316 | 71,750 |
| Example 3 | 2.360 | 2.160 | 0.100 | 0.110 | 0.277 | 0.030 | 16 | 0.250 | 0.300 | 75,377 |
| Example 4 | 2.356 | 2.160 | 0.098 | 0.110 | 0.316 | 0.030 | 16 | 0.250 | 0.306 | 89,302 |
| Example 5 | 2.360 | 2.160 | 0.100 | 0.127 | 0.307 | 0.025 | 16 | 0.250 | 0.250 | 99,998 |
| Example 6 | 2.360 | 2.160 | 0.100 | 0.110 | 0.372 | 0.030 | 16 | 0.150 | 0.300 | 101,031 |
| Example 7 | 2.360 | 2.200 | 0.080 | 0.160 | 0.464 | 0.030 | 16 | 0.150 | 0.375 | 200,547 |
| Example 8 | 2.350 | 2.200 | 0.075 | 0.160 | 0.406 | 0.025 | 16 | 0.200 | 0.333 | 238,553 |
| Example 9 | 2.393 | 2.260 | 0.067 | 0.200 | 0.528 | 0.020 | 16 | 0.150 | 0.301 | 516,794 |
| Example 10 | 2.320 | 2.200 | 0.060 | 0.210 | 0.470 | 0.015 | 16 | 0.200 | 0.250 | 711,436 |
| Example 11 | 2.360 | 2.250 | 0.055 | 0.250 | 0.523 | 0.015 | 16 | 0.200 | 0.273 | 979,726 |
| Comparative Example 7 | 2.300 | 2.200 | 0.050 | 0.210 | 0.470 | 0.015 | 16 | 0.200 | 0.300 | 1,015,636 |
| Comparative Example 8 | 2.360 | 2.260 | 0.050 | 0.250 | 0.525 | 0.015 | 16 | 0.200 | 0.300 | 1,195,413 |

Experiments for evaluating kink resistance and maneuverability of a medical instrument when a kink occurs were performed as described below using the catheters obtained through the Examples and Comparative Examples.

<Kink Resistance Evaluation Test (Loop Method)>

Figure 6:
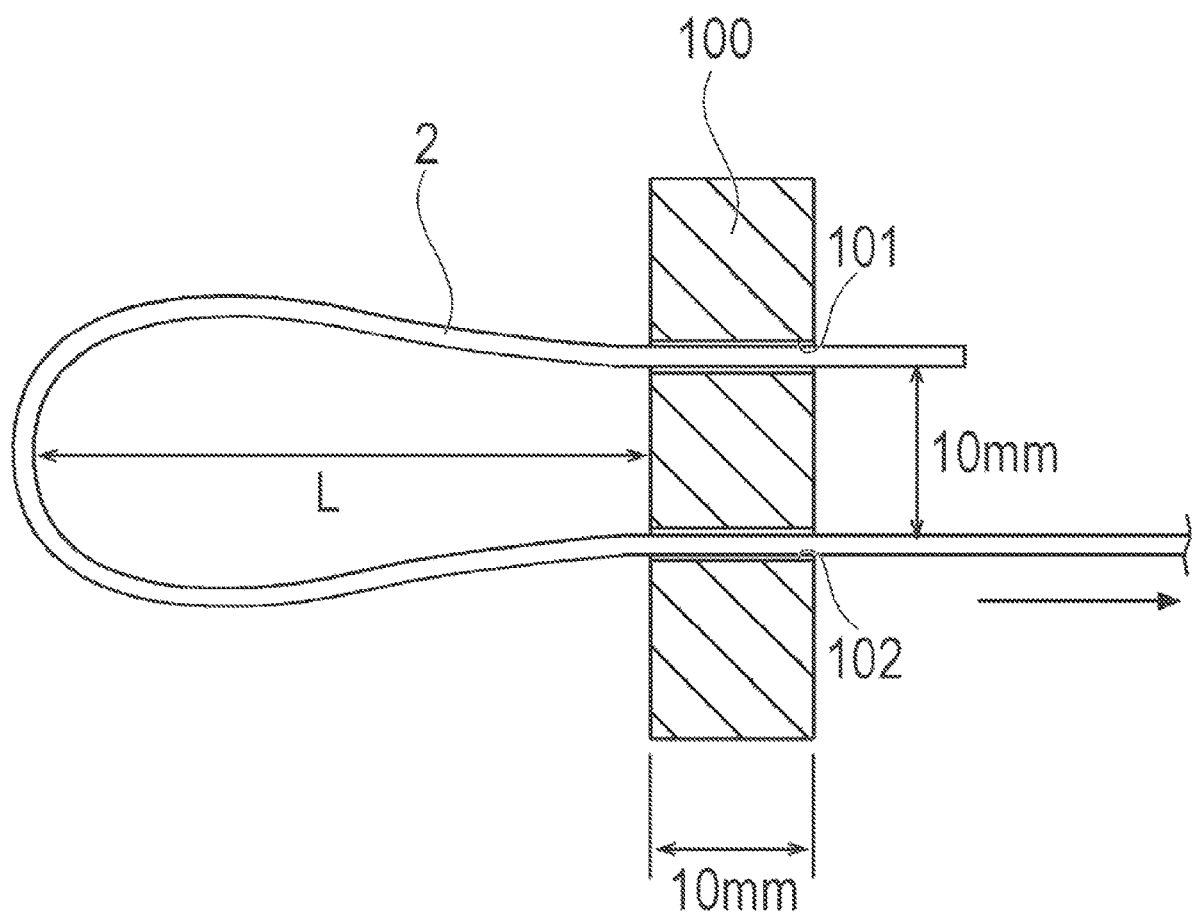
FIG. 6 is a schematic view illustrating a kink resistance evaluation test.

As illustrated in FIG. 6, a loop was made by inserting a catheter main body into two penetration holes 101 and 102 which were provided in a plate 100 having the thickness of 10 mm. The two penetration holes 101 and 102 were spaced apart from each other so as to have a center-to-center distance of 10 mm. Each of the penetration holes 101, 102 had a diameter of 2.8 mm. One end of the catheter main body was pulled so that the loop was decreased (i.e., the size of the loop protruding beyond the plate 100 decreased), and a distance L between the turned-back end of the loop and the plate 100 was measured at the time a kink occurred in the loop portion. The two penetration holes 101 and 102 were formed so as to be perpendicular to the surface of the plate 100. Note that, in this test, in order to reproduce a phenomenon inside a living body, the measurement was performed in warm water of 37° C. after the catheter main body was soaked in the warm water of 37° C. for equal to or longer than 30 minutes. As the distance L is decreased in this test, kink resistance of the catheter main body becomes relatively high and a kink is unlikely to occur.

<Maneuverability Evaluation Test>

The catheter main body of the catheter was cut into a size of 50 mm, and an intermediate portion of the catheter main body was bent and kinked once by causing the distal portion and the proximal portion of the catheter main body to come into contact with each other (causing one end of the catheter main body to be curved 180 degrees with respect to the other end of the catheter main body). Subsequently, the kinked portion of the catheter main body was returned so as to form a 90 degree angle (i.e., one end of the catheter main body was returned to form a 90 degree angle with respect to the other end of the catheter main body). This position was fixed. Thereafter, a guide wire (RADIFOCUS guide wire M, manufactured by TERUMO Corporation, 0.035 inches (0.89 mm) in outer diameter) was inserted from one end side of the lumen to verify whether or not the guide wire could successfully pass through the kinked portion.

Note that, in the maneuverability evaluation test, when the guide wire failed to pass through the lumen alone, an inner catheter (or a dilator) (1.2 mm in inner diameter) insertable into the catheter main body was inserted from one end side of the catheter main body to immediately in front of the kinked portion. Then, the guide wire was inserted into the inner catheter and was caused to protrude from the inner catheter. This allowed verification of whether or not to the guide wire succeeded in passing through the kinked portion. In this case, force causing the distal portion of the inner catheter to widen the kinked portion of the catheter main body was not applied. The inner catheter played a role of preventing (i.e., was used to prevent) the guide wire (of which the distal end was flexible and was subjected to lubrication coating) from sliding inside the catheter main body and escaping from the catheter main body. Specifically, when the guide wire slid inside the catheter main body so that force was not transmitted to the distal end of the guide wire, the inner catheter prevented the distal end of the guide wire from being bent in a direction different from the intended advancing direction.

Table 2 shows the results of each of the test. Note that, in Table 2, the Examples and Comparative Examples are arranged in ascending order of the value B.

In the maneuverability evaluation test, when the guide wire passed through the kinked portion of the catheter main body, the cross-sectional shape of the kinked portion of the catheter main body exhibited the shape illustrated in FIG. 5. Specifically, in the cross-sectional shape of the kinked portion, an inner circumferential surface of the lumen at the kinked portion in the inward direction formed a convex portion while forming an inward curved line toward the inner circumferential surface of the lumen at the kinked portion in the outward direction. Accordingly, the lumen of the catheter main body at the kinked portion formed spaces at the left radially outer end and the right radially outer end of the convex portion greater than at the center of the convex portion between the left and right radially outer ends.

TABLE 2

| | A | B | A ≥ 0.25 | 60K ≤ B < 1M | A ≥ 0.25 and 60K ≤ B < 1M | Distance L in kink resistance test result (mm) | Maneuverability test result |
|---|---|---|---|---|---|---|---|
| Comparative Example 1 | 0.313 | 55,582 | ○ | X | X | 150 | Failed in passing through |
| Comparative Example 2 | 0.188 | 55,984 | X | X | X | 200 | Failed in passing through |
| Comparative Example 3 | 0.313 | 56,783 | ○ | X | X | 150 | Failed in passing through |
| Comparative Example 4 | 0.160 | 57,370 | X | X | X | 60 | Failed in passing through |
| Comparative Example 5 | 0.194 | 57,667 | X | X | X | 45 | Failed in passing through |
| Comparative Example 6 | 0.133 | 59,022 | X | X | X | 30 | Failed in passing through |
| Example 1 | 0.350 | 63,296 | ○ | ○ | ○ | 30 | Succeeded in passing through |
| Example 2 | 0.316 | 71,750 | ○ | ○ | ○ | 40 | Succeeded in passing through |
| Example 3 | 0.300 | 75,377 | ○ | ○ | ○ | 35 | Succeeded in passing through |
| Example 4 | 0.306 | 89,302 | ○ | ○ | ○ | 37 | Succeeded in passing through |
| Example 5 | 0.250 | 99,998 | ○ | ○ | ○ | 25 | Succeeded in passing through |
| Example 6 | 0.300 | 101,031 | ○ | ○ | ○ | 30 | Succeeded in passing through |
| Example 7 | 0.375 | 200,547 | ○ | ○ | ○ | 35 | Succeeded in passing through |
| Example 8 | 0.333 | 238,553 | ○ | ○ | ○ | 45 | Succeeded in passing through |
| Example 9 | 0.301 | 516,794 | ○ | ○ | ○ | 84 | Succeeded in passing through by using inner catheter |
| Example 10 | 0.250 | 711,436 | ○ | ○ | ○ | 180 | Succeeded in passing through by using inner catheter |
| Example 11 | 0.273 | 979,726 | ○ | ○ | ○ | 300 | Succeeded in passing through by using inner catheter |
| Comparative Example 7 | 0.300 | 1,015,636 | ○ | X | X | 350 | Succeeded in passing through by using inner catheter |
| Comparative Example 8 | 0.300 | 1,195,413 | ○ | X | X | 350 | Succeeded in passing through by using inner catheter |

When the value B ranged from 55,582 to 56,783 (i.e., in Comparative Examples 1 to 3 each of which the value B was less than 60,000), the distance L became equal to or greater than 150 mm in the kink resistance evaluation test, and it was found that the value was greater and a kink was more likely to occur compared to the distances L in Examples 1 to 9. In the maneuverability evaluation test of Comparative Examples 1 to 3, the guide wire failed in passing through the kinked portion. In Comparative Examples 1 to 3, it was found that even though the catheter main body was relatively thin in wall thickness (the inner diameter was significantly large relative to the outer diameter), the value A was smaller compared to those in Examples 1 to 11, and a kink was likely to occur due to insufficient reinforcing in the radial direction (the wall thickness direction) by the reinforcements. Resultantly, the lumen inside the catheter main body at the time of being kinked was completely squashed/deformed, and the guide wire failed to pass through the lumen.

In Comparative Examples 4 to 6 in which the value B ranged from 57,370 to 59,022, the distance L ranged from 30 to 60 mm in the kink resistance evaluation test, and it was found that the value was smaller and kink resistance was higher compared to the distances L in Comparative Examples 1 to 3. In the maneuverability evaluation test of Comparative Examples 4 to 6, however, the guide wire failed to pass through the kinked portion. In Comparative Examples 4 to 6, even though the wall thickness of the catheter main body was equal to or greater than 0.125 mm (which was thicker than those in other Comparative Examples and Examples and kink resistance was higher), the value A was smaller than those in other Comparative Examples and Examples. In other words, when the catheter main body was kinked in Comparative Examples 4 to 6, the wall thickness T1 of the catheter main body was significant. Therefore, it was difficult for the guide wire to pass through the catheter main body while widening the kinked portion of the catheter main body. In the catheters in Comparative Examples 4 to 6 it was thus found that after a kink occurred, the guide wire failed to pass through.

In Examples 1 to 8 (each of which the value B ranged from 60,398 to 238,553), the distance L ranged from 25 to 45 mm in the kink resistance evaluation test. In other words, the distance L was equal to or less than 45 mm. It was found that the value was smaller and kink resistance was higher compared to the distances L in Comparative Examples 1 to 4, 7, and 8. In the maneuverability evaluation test of Examples 1 to 8, the guide wire succeeded in passing through the kinked portion. In Examples 1 to 8, the wall thickness of the catheter main body was equal to or less than 0.100 mm. This wall thickness was thinner than those in Comparative Examples 4 to 6. Since the value A was equal to or greater than 0.25 in Examples 1 to 8, reinforcing in the radial direction (the wall thickness direction) performed by the reinforcements was ensured. Moreover, since the value B ranged from 60,000 to less than 1,000,000 in Examples 1 to 8, the shape of the catheter main body was a shape unlikely to be kinked due to the value B1 included in the value B, and reinforcing in the circumferential direction (the width direction) by the reinforcements was ensured due to the value B2 included in the value B. Therefore, it was found that even after a kink occurred once, the lumen was not completely blocked so that the guide wire succeeded in passing through the kinked portion.

Among Examples 1 to 8, Examples 4 to 8 (each of which the value B ranged from 89,302 to 238,553, that is, ranged from 80,000 to less than 250,000), particularly favorable operability was found or determined. In Examples 4 to 8, it was found that because reinforcing performed by the reinforcements became stronger than those in Examples 1 to 3, the catheter main body was not too flexible, and the strength was suitable for an operation of causing the guide wire to pass through the kinked portion. Therefore, in Examples 4 to 8, the effective width W of the reinforcement 25 was equal to or greater than 0.300 mm, and the inner diameter D1 could be ensured to be equal to or greater than 2.0 mm in size.

In Examples 9 to 11 (each of which the value B ranged from 516,794 to 979,726), the distance L ranged from 84 to 300 mm in the kink resistance evaluation test. It was found that the value was greater compared to the distances L in Examples 1 to 8. Moreover, a kink was more likely to occur and kink resistance was lower compared to those in Examples 1 to 8. In the maneuverability evaluation test of Examples 9 to 11, the guide wire failed to pass through the kinked portion alone. However, the guide wire succeeded in passing through by using the inner catheter. In Examples 9 to 11, the wall thickness of the catheter main body ranged from 0.055 to 0.067 mm, and the wall thickness of the catheter main body was thinner than those in Comparative Examples 1 to 6 and Examples 1 to 8. Therefore, a kink was more likely to occur. However, even though the catheter main body was kinked, the inner catheter was used and the inner catheter served as a foothold. Accordingly, the guide wire could be easily thrust into the kinked portion. Therefore, the guide wire could pass through the catheter main body in a manner of widening the kinked portion.

In Comparative Examples 7 and 8 (each of which the value B ranged from 1,015,636 to 1,195,413, that is equal to or greater than 1,000,000), the distance L was 350 mm in the kink resistance evaluation test. It was found that the value was greater, a kink was more likely to occur, and kink resistance was low compared to those in other Examples and Comparative Examples. In the maneuverability evaluation test of Comparative Examples 7 and 8, the guide wire failed to pass through the kinked portion by itself. However, the guide wire succeeded in passing through by using the inner catheter. In Examples 9 to 11, the wall thickness of the catheter main body was 0.050 mm which was thinner than those in other Examples and Comparative Examples, and it was found that a kink was more likely to occur and unless the inner catheter was used, the guide wire could not pass through the kinked portion. In addition, in Comparative Examples 7 and 8, due to the catheter main body which was excessively thin in wall thickness, when the catheter was kinked, a phenomenon in which the reinforcements were protruding from the catheter main body was found.

The catheter and method of manufacturing the catheter disclosed here are not limited to the embodiments described above, and various changes can be made by those skilled in the art within the technical scope and gist of the catheter and method disclosed here. For example, the purpose of the catheter is not particularly limited as long as the catheter is used by being inserted into a biological lumen of a living body. The biological lumen is not limited to a blood vessel. For example, the biological lumen may be a vas, the ureter, the bile duct, the oviduct, and the hepatic duct. Particularly, in the technique of TRI, the catheter needs to be delivered to a blood vessel of the lower extremity via the radial artery, the subclavian artery, and the like. When a blood vessel of the lower extremity is a treatment site, a blood vessel which becomes a treatment target is the iliac artery and the femoral artery, for example. Therefore, for example, there is a possibility that the catheter is kinked at a curved portion of a blood vessel between the subclavian artery and the thoracic aorta. Therefore, the catheter disclosed here is suitable for a case of treating a blood vessel of the lower extremity through the technique of TRI.

In addition, the catheter main body may be configured such that flexibility gradually increases in the direction toward the distal end. Accordingly, when performing an insertion operation with respect to a blood vessel, it is possible to help ensure sufficient pushability and torque transmission toward the distal side and to more safely perform insertion with respect to a blood vessel. The outer layer or the inner layer can be divided into multiple regions in the axial direction, the shape or the material of the region on the distal side can be varied so as to be flexible, and the dimensions or the pitch of the reinforcements can be changed such that flexibility of the catheter main body gradually increases in the direction toward the distal end.

In addition, the inner layer and the outer layer of the catheter main body may be integrally formed from the same material.

The detailed description above describes a catheter, a method of manufacturing a catheter and a method of using a catheter. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A method comprising:
   inserting a catheter into a blood vessel of an arm of a living body, the catheter comprising:
     an inner layer forming an inner surface of a tubular catheter main body having a lumen;
     an outer layer forming an outer surface of the catheter main body, the catheter main body possessing an inner diameter, an outer diameter and a wall thickness;
     multiple reinforcements embedded between the inner surface and the outer surface of the catheter main body; and
   the catheter satisfying Expressions (1), (2), (3), (4), (5), and (6) below:

$0.050 \text{ mm} \leq T1 \leq 0.100 \text{ mm}$  Expression (1)

$T2/T1 \geq 0.25$  Expression (2)

$60{,}000 \leq (D1 \times D2 \times W \times N)/(T1^2 \times T2) < 1{,}000{,}000$  Expression (3)

$B1 = (D1/T1) \times (D2/T1)$  Expression (4)

$B2 = (W \times N)/T2$  Expression (5)

$B = B1 \times B2$  Expression (6), wherein the inner diameter of the catheter main body is D1, the outer diameter of the catheter main body is D2, the wall thickness of the catheter main body is T1, a thickness of each reinforcement along a radial direction of the catheter main body is T2, an effective width of each reinforcement along the circumferential direction of the catheter main body in a cross section orthogonal to an axial direction of the catheter main body is W, and a total number of the multiple reinforcements is N, the outer diameter of the catheter main body being 2.32 mm to 3 mm, and
   the value B being 80,000 to less than 500,000;
   advancing the catheter from the arm of the living body toward a blood vessel in a lower extremity of the living body; and
   positioning the distal end of the catheter in the blood vessel in the lower extremity of the living body.

2. The method according to claim 1, wherein the catheter main body is linear throughout an axial extent of the catheter main body before the inserting of the catheter into the blood vessel of the arm of the living body.

3. The method according to claim 1, wherein the inner diameter D1 of the catheter main body is 1.85 mm-2.26 mm.

4. The method according to claim 1, wherein each of the reinforcements is a helically-wound reinforcement.

5. The method according to claim 1, wherein: i) the total number of the multiple reinforcements is at least 8 and not greater than 32; ii) the effective width W of each reinforcement is at least 0.200 mm and no greater than 0.600 mm; and iii) each of the reinforcements possesses a pitch of at least 1.5 mm and no greater than 7.0 mm.

6. The method according to claim 1, wherein the multiple reinforcements are embedded within only the outer layer of the catheter main body.

7. A method comprising:
   inserting a catheter into a radial artery of a living body, the catheter comprising:
     an inner layer forming an inner surface of a tubular catheter main body having a lumen, an outer layer forming an outer surface of the catheter main body, the catheter main body possessing an inner diameter, an outer diameter, a distal end, and a wall thickness, multiple reinforcements between the inner surface and the outer surface of the catheter main body, and the catheter satisfying Expressions (1), (2), and (3) below:

$0.050 \text{ mm} \leq T1 \leq 0.100 \text{ mm}$  Expression (1)

$T2/T1 \geq 0.25$  Expression (2)

$60{,}000 \leq (D1 \times D2 \times W \times N)/(T1^2 \times T2) < 1{,}000{,}000$  Expression (3), wherein the inner diameter of the catheter main body is D1, the outer diameter of the catheter main body is D2, the wall thickness of the catheter main body is T1, a thickness of each reinforcement along a radial direction of the catheter main body is T2, an effective width of each reinforcement along the circumferential direction of the catheter main body in a cross section orthogonal to an axial direction of the catheter main body is W, and a total number of the multiple reinforcements is N;
   advancing the catheter from the radial artery toward a blood vessel in a lower extremity of the living body;
   positioning the distal end of the catheter at a target site in the blood vessel in the lower extremity of the living body; and
   determining a kink exists along the catheter while the distal end of the catheter is in the blood vessel in the lower extremity of the living body; and
   introducing a guide wire into the catheter when a kink is determined to exist along the catheter and advancing the guide wire through the kink.

8. The method according to claim 7, wherein the positioning of the distal end of the catheter at the target site in the blood vessel in the lower extremity of the living body includes positioning the distal end of the catheter at the target site in the iliac artery or the femoral artery.

9. The method according to claim 7, wherein the positioning of the distal end of the catheter at the target site in the blood vessel in the lower extremity of the living body includes positioning the distal end of the catheter at a stenosed target site in the iliac artery or the femoral artery.

10. The method according to claim 9, further comprising introducing a treatment catheter into the catheter after the introducing of the guide wire into the catheter and the advancing of the guide wire through the kink.

11. The method according to claim 10, wherein the introducing of the treatment catheter into the catheter comprises introducing: i) a dilation catheter; or ii) a stent transporting catheter through which a stent is transported to a stenosed site.

12. The method according to claim 7, further comprising introducing a treatment catheter into the catheter after the introducing of the guide wire into the catheter and the advancing of the guide wire through the kink.

13. The method according to claim 7, wherein the catheter main body is linear throughout an axial extent of the catheter main body before the inserting of the catheter into the radial artery of the living body.

14. The method according to claim 7, wherein the multiple reinforcements are embedded within only the outer layer of the catheter main body.

* * * * *